United States Patent
Rexhausen et al.

(10) Patent No.: US 6,438,427 B1
(45) Date of Patent: Aug. 20, 2002

(54) DILATABLE CARDIAC ELECTRODE ARRANGEMENT FOR IMPLANTATION IN PARTICULAR IN THE CORONARY SINUS OF THE HEART

(75) Inventors: Hermann Rexhausen, deceased, late of Berlin; Alfred Joseph Zmarzlik, legal representative, Eschweiler; by Johannes Oskar Schulz, legal representative, Torstberg; by Dietmar Schulz, legal representative, Essen; Dieter Hermann Schulz, legal representative; Maria Barbara Schulz, legal representative, both of Düsseldorf; by Rodewald (Helmut) Schulz, legal representative, Hildesheim; by Oskar Josef Schulz, legal representative, Bonn; by Edith Maria Galisch, legal representative, Hildesheim; by Johanna Magdalene Polinowski, legal representative; by Waltraud Sieglinde Schulz, legal representative, both of Dortmund; by Margarete Speck, legal representative, Frankfurt am Main, all of (DE); Luc Jordaens, Rotterdam (NL)

(73) Assignee: Biotronik Mess-und Therapiegerate GmbH & Co. Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/531,440

(22) Filed: Mar. 20, 2000
  (Under 37 CFR 1.47)

(30) Foreign Application Priority Data

Mar. 20, 1999 (DE) ............................... 199 12 635

(51) Int. Cl.$^7$ ................................................ A61N 1/05
(52) U.S. Cl. ........................ 607/126; 607/119; 607/122
(58) Field of Search ............................... 600/372–374, 600/381; 606/191, 194, 198; 607/115, 116, 119, 122, 123, 126; 623/1.1, 1.15

(56) References Cited

U.S. PATENT DOCUMENTS

| | | | |
|---|---|---|---|
| 5,170,802 A | | 12/1992 | Mehra |
| 5,360,440 A | * | 11/1994 | Andersen ..................... 607/116 |
| 5,411,546 A | * | 5/1995 | Bowald et al. ............. 607/126 |
| 5,423,772 A | | 6/1995 | Lurie et al. |
| 5,433,730 A | * | 7/1995 | Alt ................................ 607/5 |
| 5,531,779 A | | 7/1996 | Dahl et al. |
| 5,954,761 A | * | 9/1999 | Machek et al. ............. 607/126 |
| 6,161,029 A | * | 12/2000 | Spregil et al. .............. 600/381 |

* cited by examiner

Primary Examiner—Kennedy Schaetzle
Assistant Examiner—Kristen Droesch
(74) Attorney, Agent, or Firm—Browdy and Neimark

(57) ABSTRACT

A dilatable cardiac electrode arrangement for implantation in particular in the coronary sinus of the heart is provided with a defibrillator electrode of the type of a stent and of an expandable, electrically conductive structure; with annular pacemaker electrodes; with insulation zones between the pacemaker electrodes on the one hand and the defibrillator electrode on the other; and with electric lines for the defibrillator and pacemaker electrodes.

10 Claims, 1 Drawing Sheet

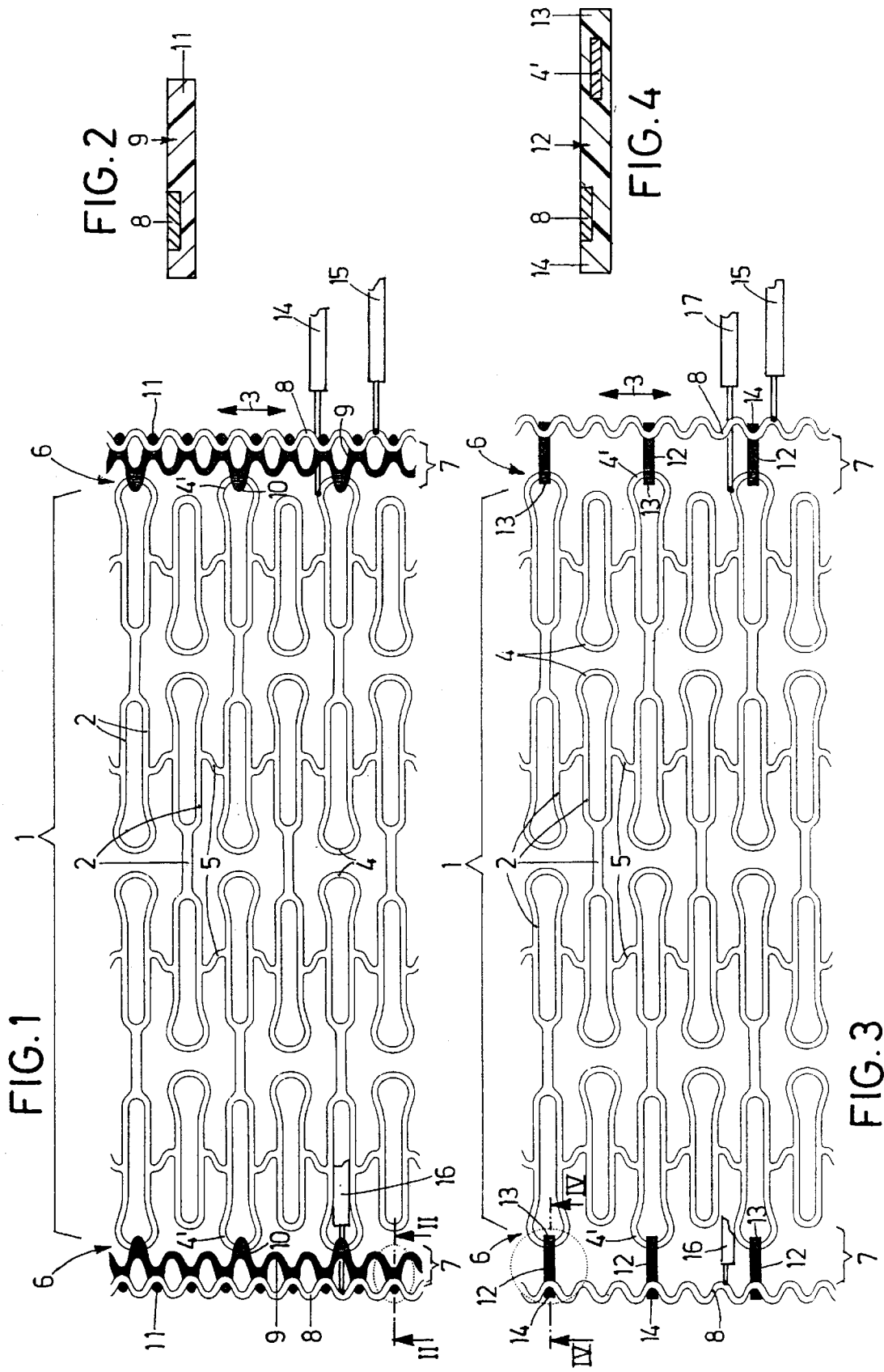

DILATABLE CARDIAC ELECTRODE ARRANGEMENT FOR IMPLANTATION IN PARTICULAR IN THE CORONARY SINUS OF THE HEART

BACKGROUND OF THE INVENTION

1. Field of the Invention

The invention relates to a dilatable cardiac electrode arrangement for implantation in particular in the coronary sinus of the heart.

2. Background Art

As for the background of the invention, it can be said that fundamentally, cardiac pacemakers and defibrillators, by their electrode arrangements, take access to the right ventricle of the heart. On the one hand, this is due to the better accessibility of the right ventricles for corresponding electrode catheters, on the other hand the sinoatrial node tissue as a natural pacemaker of the healthy heart is also located in the right portion of the heart, namely in the area of the right atrium.

The left ventricles are badly accessible for conventional transvenous electrode implantation procedures. Since the stimulation of the myocardium spreads automatically to the other side of the heart, measuring and stimulation via electrode arrangements that are implanted in the right ventricle will as a rule be sufficient.

However, the right ventricles only attend to the pulmonary circulation of smaller volume and are therefore dimensioned smaller than the left ventricles. Consequently, they participate only to a reduced extent in the total heart pumping capacity. Owing to the difference in dimension and importance of the right and the left half of the heart, there is a fundamental interest, from a cardiologic point of view, to have direct access by corresponding electrode arrangements also to the left side of the heart. For instance, the time lapse of stimulus propagation from the right to the left side of the heart can thus be stated. Furthermore, certain forms of tachycardiac arrythmia can be combated by corresponding electrode arrangements on the left side of the heart, such as disorders in which the stimulation of the myocardium passes in a circuit through the left atrium, both ventricles, the right atrium, the left atrium etc. Such tachycardiac arrythmias can be diagnosed at an early stage from the accompanying overlong periods of stimulus conduction between the left and the right atrium.

Typically, the left atrium of the heart and—with certain reservations—also the left ventricle can be reached by electrode arrangements which are implanted in the coronary sinus on the left side of the heart. To this end, various prior art suggestions have been made.

For instance, a pacemaker electrode is known from U.S. Pat. No. 5,423,772, having three portions of varying rigidity, namely a main reinforced portion, an intermediate zone portion and a soft tip portion. The end of this catheter that can be introduced into the coronary sinus further comprises two curved portions of a greater radius of curvature upstream of the tip and a smaller radius of curvature at the tip. The first curvature provides for the electrode to be fixed mechanically in the coronary sinus, whereas the hooked end improves the angle and the pressure, relative to the wall of the coronary sinus, of a tip electrode disposed on the tip of the catheter.

As regards the number of electrodes and their placement on the body of the catheter, U.S. Pat. No. 5,423,772 illustrates, in addition to the tip electrode, only some further annular electrodes of approximately the same size, the number of which is specified to be ten or more. The number of electrodes and their placement is intended to comply with the respective sensing purposes of the electrode arrangement.

Problems in the implantation of electrode catheters in particular in the coronary sinus reside in that the implanted catheter leads to stenosis of the vessel cross section and thus to a restriction in the flow of blood, which means a considerable drawback in the supply to the heart.

To solve these problems, U.S. Pat. No. 5,170,802 proposes a dilatable electrode arrangement for implantation in particular in the coronary sinus of the heart, in which one or several electrodes are provided, which are expandable in the way of a stent and are coupled to individual conductors or to a common collective conductor. Dilatation of the electrode arrangement may take place—as known from vessel wall supports or "stents"—by a balloon catheter or by a spring design of the electrode structure. In terms of fact, U.S. Pat. No. 5,170,802 discloses a defibrillation electrode.

Finally, U.S. Pat. No. 5,531,779 teaches a defibrillation electrode of the type of a stent, the electrode body of which consists of individual wire filaments which, in the expanded condition, form sort of a closed basket. The ends of these wire filaments are collected by ring or cap type tops of electrically conductive material and thus fixed mechanically. The conductor of the electrode is electrically connected via one of the two caps on the ends.

SUMMARY OF THE INVENTION

It is an object of the invention to improve the functionality of dilatable heart electrode arrangements for implantation in particular in the coronary sinus of the heart and in particular to create a combined defibrillator and pacemaker electrode for the coronary sinus.

This object is attained in a dilatable cardiac electrode arrangement for implantation in particular in the coronary sinus of the heart, comprising a defibrillator electrode of the type of a stent having an expandable, electrically conductive structure; pacemaker electrodes in the form of a circle or a section of a circle, which have a smaller surface as compared to the defibrillator electrode, and which are disposed on the ends, facing away from each other, of the defibrillator electrode, and which also have an electrically conductive structure which is expandable in the way of a stent; insulation zones between the pacemaker electrodes on the one hand and the defibrillator electrode on the other; and electric lines for the defibrillator and pacemaker electrodes. Correspondingly, provision is made for a defibrillator electrode of the type of a stent having an expandable and electrically conductive structure on the one hand and for two pacemaker electrodes on the other hand, which have a smaller surface as compared to the defibrillation electrode and are disposed on the ends, facing away from each other, of the defibrillator electrode and also have an electrically conductive structure which is expandable in the way of a stent. Insulation zones are provided between the pacemaker electrodes on the one hand and the defibrillator electrode on the other. They serve for electrically insulating the mentioned electrodes from each other and moreover produce the mechanical connection between the individual electrodes. Finally, electric lines are provided for the defibrillator and pacemaker electrodes. The term "in the form of a section of a circle" means a divided annular electrode, in which only peripheral sections serve as a sensing electrode.

As a result of the design, according to the invention, of a cardiac electrode arrangement, electrode implants of combined defibrillator and pacemaker functionality can be inserted also in the area of the left side of the heart at a reasonable implantation expenditure.

Details of the invention will become apparent from the ensuing description of preferred exemplary embodiments, taken in conjunction with the drawing.

BRIEF DESCRIPTION OF THE DRAWING

FIG. 1 is a developed view of a detail of a first embodiment of a dilatable cardiac electrode arrangement;

FIG. 2 is a partial sectional view of the arrangement on the line II—II of FIG. 1;

FIG. 3 is a developed view of a detail of a second embodiment of a dilatable cardiac electrode arrangement; and FIG. 4 is partial sectional view of the arrangement on the line IV—IV of FIG. 3.

DESCRIPTION OF THE PREFERRED EMBODIMENTS

In the embodiment, seen in FIG. 1, of the cardiac electrode arrangement, a central defibrillator electrode 1 of the type of a stent is provided, which has a reticular rib structure known from stents or so-called vessel wall supports. The rib structure comprises lengthwise ribs 2, which branch and which, in the implanted condition, are parallel to the direction of flow of the blood in the vessel. Crosswise ribs are integrally connected therewith; they run substantially in the peripheral direction 3 and, working as arching ribs 4, they join the lengthwise ribs 2 at their ends. On the other hand, crosswise ribs working as connecting ribs 5 extend between lengthwise ribs 2 which lie side by side, thus producing the reticular structure. The defibrillator electrode 1 is integrally manufactured from medically well tolerated, thin sheet metal by punching, laser beam or water jet cutting.

Provided at the two lengthwise ends 6 are insulation zones designated in their entirety by 7, via which the pacemaker electrodes 8 located on the ends are connected. By analogy to the defibrillator electrode 1, they extend annularly in the peripheral direction 3 and have a wavy configuration. They are also cut from thin metal sheet by the aid of the above-mentioned working processes. As seen in FIG. 1, the pacemaker electrodes 8 have a surface which is smaller by orders of magnitude as compared to the defibrillator electrode.

In the embodiment according to FIGS. 1 and 2, the insulation zones 7 are formed as continuous insulation bridges 9 of electrically insulating polymeric material. Each of these insulation bridges 9 consists of a wavy polymer strand which extends in the peripheral direction 3. The inward wave crests 10 of the strand are cast to enclose the external arching ribs 4' of the defibrillator electrode 1. By analogy, the outward wave crests 11 of the two insulation bridges 9 are connected to the wavy pacemaker electrodes 8 by being cast on the inward wave crests of thereof. The polymer strand, which constitutes the insulation bridge 9 and which is very filigree as compared to the strongly enlarged illustration of the attached figures, can be produced by a circular belt being cast on and by subsequent etching and polishing.

As regards the design of the defibrillator electrode 1 and the two pacemaker electrodes 8, the version seen in FIGS. 3 and 4 of an electrode arrangement according to the invention does not differ from the embodiment according to FIGS. 1 and 2. In this regard, reference is made to the description of this embodiment. Identical components have identical reference numerals in FIGS. 3 and 4.

The difference between the two embodiments only resides in that the insulation zone 7 of the electrode arrangement according to FIGS. 3 and 4 is formed by individual bridging ribs 12 distributed along the periphery of the electrode arrangement. By their ends 13, these bridging ribs 12 are cast on the outside, marginally arching ribs 4' of the defibrillator electrode 1. By the second end 14, each bridging rib 12 is cast on an inward wave crest of the encircling, wavy pacemaker electrode 8.

In both embodiments, contacting the defibrillator and pacemaker electrode 1, 8 takes place by electric lines 14, 15, 16. They are piloted in a thin catheter (not seen in the drawing). The electrically conductive cores of the electric lines 14, 15, 16 should be so-called cables—not outlined in detail—which are more flexible and have a smaller diameter than the helixes frequently used as conductors in catheters. This is of major importance in particular with regard to the use of the electrode arrangement according to the invention in small blood vessels, such as the coronary sinus, because of the reduced irritation of the vessel walls and the minimized obstruction of the flow of blood. As a rule, these cables comprise few strands of so-called medical steel (MP 35 N) or strands of high-grade steel with a silver core (DFT=Drawn Filed Tube).

As regards the contacting, special attention must be directed to the distal pacemaker electrode—which is the left pacemaker electrode 8 in FIGS. 1 and 3. This line 16 must be guided electrically insulated over the entire length of the defibrillator electrode 1 of the type of a stent. To this end, three variants are conceivable, namely a position completely outside, a position completely inside or a variant in which the line is braided through the individual ribs 4, 5. From a point of view of manufacture and implantation, the variant positioned completely outside must be preferred. Guidance of the line completely inside involves problems, because this line may be damaged upon dilatation of the stent type electrode arrangement at a pressure of 8 to 12 bar or it may become detached from the respective electrode at its point of contact therewith. Consequently, the line might get into, and interfere with, the flow of blood. The braided variant does not pose any problems regarding the electric insulation of the points of fixing of the line on the electrode.

Both embodiments are illustrated in a non-dilated condition in FIGS. 1 and 3. Upon expansion of a balloon catheter towards dilatation, the curved connecting ribs 5 between lengthwise ribs 2 that lie side by side are straightened, whereby the defibrillator electrode 1 expands, taking its rest on the inside wall of the coronary sinus. A similar stretching and straightening effect can be observed in the wavy pacemaker electrodes 8 and the wavy insulation bridges 9 in the embodiment according to FIG. 1. In the embodiment according to FIG. 3, the individual bridging ribs 12 are spaced from each other upon dilatation.

In conclusion, attention is drawn to the fact that the insulation zones need not necessarily be made from polymeric material as in the embodiments according to the attached FIGS. 1 to 4. There is the possibility to manufacture the entire electrode arrangement in a single piece from electrically conductive material, after which the insulation zones 7 between the defibrillator and the pacemaker electrodes 1, 8 are rendered electrically insulating by heat treatment or ion implantation of the material. In this way, an especially homogeneous electrode structure can be obtained, which positively affects the introduction behavior and long-term tolerance of the electrode arrangement.

What is claimed is:

1. A dilatable cardiac electrode arrangement for implantation in particular in a coronary sinus of the heart; comprising a defibrillator electrode (1) having an expandable, electrically conductive structure and having two ends that face away from one another;

pacemaker electrodes (8) in the form of at least a section of a ring,
which have a smaller surface as compared to the defibrillator electrode (1),
which are disposed on said ends (6) of the defibrillator electrode (1), and
which also have an electrically conductive structure which is expandable from a first diameter to a second diameter, the second diameter being larger than the first diameter;

insulation zones (7) between the pacemaker electrodes (8) and the defibrillator electrode (1); and electric liens (15, 16, 17) for the defibrillator electrode (1) and the pacemaker electrodes (8).

2. An electrode arrangement according to claim 1, wherein the defibrillator electrode (1) consists of a reticular rib structure of lengthwise ribs (2) and crosswise ribs (4, 4', 5, 5') which are integrally connected therewith and extend substantially in a peripheral direction (3).

3. An electrode arrangement according to claim 1, wherein the pacemaker electrodes (8) comprise at least one wavy rib extending in a peripheral direction (3).

4. An electrode arrangement according to claim 1, wherein the insulation zones (7) are formed by insulation bridges (9) of electrically insulating polymeric material.

5. An electrode arrangement according to claim 4, wherein the defibrillator electrode (1) comprises marginal ribs (4') and the insulation bridges (9) are formed by a wavy polymer strand which extends in a peripheral direction and is joined to said marginal ribs (4') of the defibrillator electrode (1) and the pacemaker electrodes (8) by casting.

6. An electrode arrangement according to claim 4, wherein the defibrillator electrode (1) comprises marginal ribs (4') and the insulation bridges (9) are formed by individual bridging ribs (12) with ends (13, 14), which ribs (12) are distributed over the circumference of the electrode arrangement; and wherein the ends (13, 14), facing away from each other, of the ribs (12) are joined by casting to the marginal ribs (4') of the defibrillator electrode (1) and to the pacemaker electrode (8).

7. An electrode arrangement according to claim 1, wherein the entire electrode arrangement is manufactured integrally from electrically conductive material, the insulation zones between defibrillator and pacemaker electrodes being rendered electrically insulating by one of heat treatment and ion implantation of the material.

8. An electrode arrangement according to claim 1, wherein the two pacemaker electrodes (8) jointly form a bipolar pacemaker electrode arrangement.

9. An electrode arrangement according to claim 1, wherein the electric lines (15, 16, 17) comprise cores which are thin cables.

10. An electrode arrangement according to claim 1, wherein at least the electric line (16) that contacts one of the pacemaker electrodes (8) is guided completely outside along the cardiac electrode arrangement.

* * * * *